(12) United States Patent
Heidner

(10) Patent No.: US 7,201,763 B2
(45) Date of Patent: Apr. 10, 2007

(54) DISTAL BALLOON WAIST MATERIAL RELIEF AND METHOD OF MANUFACTURE

(75) Inventor: Matthew Heidner, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 421 days.

(21) Appl. No.: 10/032,962

(22) Filed: Oct. 24, 2001

(65) Prior Publication Data

US 2003/0078613 A1    Apr. 24, 2003

(51) Int. Cl.
*A61M 25/10* (2006.01)

(52) U.S. Cl. ...................... 606/194; 604/103

(58) Field of Classification Search ........... 264/156, 264/248; 604/103, 103.06, 103.08; 606/194
See application file for complete search history.

(56) References Cited

U.S. PATENT DOCUMENTS

| | | |
|---|---|---|
| 3,911,927 A | 10/1975 | Rich et al. |
| 4,085,185 A | 4/1978 | Adair |
| 4,195,637 A | 4/1980 | Grüntzig et al. |
| 4,249,536 A | 2/1981 | Vega |
| 4,251,305 A | 2/1981 | Becker et al. |
| 4,307,722 A | 12/1981 | Evans |
| 4,385,635 A | 5/1983 | Ruiz |
| 4,413,989 A | 11/1983 | Schjeldahl et al. |
| 4,425,919 A | 1/1984 | Alston, Jr. et al. |
| 4,456,000 A | 6/1984 | Schjeldahl et al. |
| 4,490,421 A | 12/1984 | Levy |
| 4,531,512 A | 7/1985 | Wolvek et al. |
| 4,531,943 A | 7/1985 | Van Tassel et al. |
| 4,540,404 A | 9/1985 | Wolvek |
| 4,551,292 A | 11/1985 | Fletcher et al. |
| 4,588,399 A | 5/1986 | Nebergall et al. |
| 4,596,563 A | 6/1986 | Pande |
| 4,636,272 A | 1/1987 | Riggs |
| 4,636,346 A | 1/1987 | Gold et al. |
| 4,646,719 A | 3/1987 | Neuman et al. |
| 4,676,229 A | 6/1987 | Krasnicki et al. |
| 4,706,670 A | 11/1987 | Andersen et al. |
| 4,739,768 A | 4/1988 | Engelson |
| 4,748,982 A | 6/1988 | Horzewski et al. |
| 4,753,765 A | 6/1988 | Pande |
| 4,759,748 A | 7/1988 | Reed |
| 4,764,324 A | 8/1988 | Burnham |

(Continued)

FOREIGN PATENT DOCUMENTS

EP      0 171 884 A1    2/1986

(Continued)

OTHER PUBLICATIONS

TG-12-X3 Centerless Grinder (Date Unknown), one sheet.

(Continued)

*Primary Examiner*—Michael Thaler
(74) *Attorney, Agent, or Firm*—Crompton, Seager & Tufte, LLC

(57) ABSTRACT

A balloon catheter having an improved balloon waist design in which material is removed prior to thermal processing. In one embodiment, a series of patterned voids are formed in the balloon waist to reduce the amount of polymeric material and to better control flowing polymeric material during thermal processing.

11 Claims, 2 Drawing Sheets

U.S. PATENT DOCUMENTS

| | | |
|---|---|---|
| 4,782,834 A | 11/1988 | Maguire et al. |
| 4,808,164 A | 2/1989 | Hess |
| 4,817,613 A | 4/1989 | Jaraczewski et al. |
| 4,819,751 A | 4/1989 | Shimada et al. |
| 4,820,349 A | 4/1989 | Sabb |
| RE32,983 E | 7/1989 | Levy |
| 4,863,442 A | 9/1989 | DeMello et al. |
| 4,884,573 A | 12/1989 | Wijay et al. |
| 4,886,506 A | 12/1989 | Lovgren et al. |
| RE33,166 E | 2/1990 | Samson |
| 4,898,896 A | 2/1990 | Maj et al. |
| 4,906,241 A | 3/1990 | Noddin et al. |
| 4,906,244 A | 3/1990 | Pinchuk et al. |
| 4,917,666 A | 4/1990 | Solar et al. |
| 4,323,071 A | 5/1990 | Simpson et al. |
| 4,323,071 A | 5/1990 | Simpson et al. |
| 4,921,483 A | 5/1990 | Wijay et al. |
| 4,943,278 A | 7/1990 | Euteneuer et al. |
| 4,955,377 A | 9/1990 | Lennox et al. |
| 4,955,862 A | 9/1990 | Sepetka |
| 4,960,410 A | 10/1990 | Pinchuk |
| 4,963,313 A | 10/1990 | Noddin et al. |
| 4,964,409 A | 10/1990 | Tremulis |
| 4,964,853 A | 10/1990 | Sugiyama et al. |
| 4,976,720 A | 12/1990 | Machold et al. |
| 4,994,018 A | 2/1991 | Saper |
| 4,994,032 A | 2/1991 | Sugiyama et al. |
| RE33,561 E | 3/1991 | Levy |
| 4,998,923 A | 3/1991 | Samson et al. |
| 5,002,559 A | 3/1991 | Tower |
| 5,047,045 A | 9/1991 | Arney et al. |
| 5,050,606 A | 9/1991 | Termulis |
| 5,078,702 A | 1/1992 | Pomeranz |
| 5,078,727 A | 1/1992 | Hannam et al. |
| 5,087,394 A | 2/1992 | Keith |
| 5,093,546 A | 3/1992 | Matsumiya et al. |
| 5,100,381 A | 3/1992 | Burns |
| 5,108,415 A | 4/1992 | Pinchuk et al. |
| 5,120,308 A | 6/1992 | Hess |
| 5,122,125 A | 6/1992 | Deuss |
| 5,139,496 A | 8/1992 | Hed |
| 5,143,093 A | 9/1992 | Sahota |
| 5,147,377 A | 9/1992 | Sahota |
| 5,154,725 A | 10/1992 | Leopold |
| 5,156,594 A | 10/1992 | Keith |
| 5,156,612 A | 10/1992 | Pinchuk et al. |
| 5,158,548 A | 10/1992 | Lau et al. |
| 5,159,937 A | 11/1992 | Tremulis |
| 5,163,989 A | 11/1992 | Campbell et al. |
| 5,171,230 A | 12/1992 | Eland et al. |
| 5,176,637 A | 1/1993 | Sagae |
| 5,180,585 A | 1/1993 | Jacobson et al. |
| 5,209,728 A | 5/1993 | Kraus et al. |
| 5,213,574 A | 5/1993 | Tucker |
| 5,221,270 A | 6/1993 | Parker |
| 5,226,888 A | 7/1993 | Arney |
| 5,234,416 A | 8/1993 | Macaulay et al. |
| 5,240,537 A | 8/1993 | Bodicky |
| 5,254,091 A | 10/1993 | Aliahmad et al. |
| 5,256,144 A | 10/1993 | Kraus et al. |
| 5,256,145 A | 10/1993 | Atkinson et al. |
| 5,258,160 A | 11/1993 | Utsumi et al. |
| 5,259,839 A | 11/1993 | Burns |
| 5,270,086 A | 12/1993 | Hamlin |
| 5,279,561 A | 1/1994 | Roucher et al. |
| 5,279,562 A | 1/1994 | Sirhan et al. |
| 5,304,134 A | 4/1994 | Kraus et al. |
| 5,304,198 A | 4/1994 | Samson |
| 5,304,340 A | 4/1994 | Downey |
| 5,316,706 A | 5/1994 | Muni et al. |
| 5,318,032 A | 6/1994 | Lonsbury et al. |
| 5,318,527 A | 6/1994 | Hyde et al. |
| 5,318,532 A | 6/1994 | Frassica |
| 5,324,259 A | 6/1994 | Taylor et al. |
| 5,324,263 A | 6/1994 | Kraus et al. |
| 5,328,468 A | 7/1994 | Kaneko et al. |
| 5,334,146 A | 8/1994 | Ozasa |
| 5,334,148 A | 8/1994 | Martin |
| 5,334,168 A | 8/1994 | Hemmer |
| 5,335,410 A | 8/1994 | Burnham |
| 5,342,386 A | 8/1994 | Trotta |
| 5,344,400 A | 9/1994 | Kaneko et al. |
| 5,346,505 A | 9/1994 | Leopold |
| 5,358,486 A | 10/1994 | Saab |
| 5,370,615 A | 12/1994 | Johnson |
| 5,370,655 A | 12/1994 | Burns |
| 5,387,193 A | 2/1995 | Miraki |
| 5,389,087 A | 2/1995 | Miraki |
| 5,397,306 A | 3/1995 | Nobuyoshi et al. |
| 5,399,164 A | 3/1995 | Snoke et al. |
| 5,403,292 A | 4/1995 | Ju |
| 5,405,338 A | 4/1995 | Kranys |
| 5,411,477 A | 5/1995 | Saab |
| 5,415,635 A | 5/1995 | Bagaoisan et al. |
| 5,423,754 A | 6/1995 | Cornelius et al. |
| 5,425,709 A | 6/1995 | Gambale |
| 5,425,712 A | 6/1995 | Goodin |
| 5,443,495 A | 8/1995 | Buscemi et al. |
| 5,447,497 A | 9/1995 | Sogard et al. |
| 5,454,795 A | 10/1995 | Samson |
| 5,458,613 A | 10/1995 | Gharibadeh et al. |
| 5,470,313 A | 11/1995 | Crocker et al. |
| 5,470,322 A | 11/1995 | Horzewski et al. |
| 5,480,383 A | 1/1996 | Bagnoisan et al. |
| 5,496,271 A | 3/1996 | Burton et al. |
| 5,496,294 A | 3/1996 | Hergenrother et al. |
| 5,503,263 A | 4/1996 | Watanabe |
| 5,509,910 A | 4/1996 | Lunn |
| 5,512,051 A | 4/1996 | Wang et al. |
| 5,514,092 A | 5/1996 | Forman et al. |
| 5,531,715 A | 7/1996 | Engelson et al. |
| 5,538,513 A | 7/1996 | Okajima |
| 5,540,236 A | 7/1996 | Ginn |
| 5,542,924 A | 8/1996 | Snoke et al. |
| 5,542,937 A | 8/1996 | Chee et al. |
| 5,549,552 A | 8/1996 | Peters et al. |
| 5,549,556 A | 8/1996 | Ndondo-Lay et al. |
| 5,554,121 A | 9/1996 | Ainsworth et al. |
| 5,554,139 A | 9/1996 | Okajima |
| 5,556,383 A | 9/1996 | Wang et al. |
| 5,569,200 A | 10/1996 | Umeno et al. |
| 5,569,218 A | 10/1996 | Berg |
| 5,587,125 A | 12/1996 | Roychowdhury |
| 5,591,129 A * | 1/1997 | Shoup et al. ............ 604/103.1 |
| 5,605,543 A | 2/1997 | Swanson |
| 5,643,209 A | 7/1997 | Fugoso et al. |
| 5,645,528 A | 7/1997 | Thome |
| 5,649,908 A | 7/1997 | Itoh |
| 5,649,909 A * | 7/1997 | Cornelius ............... 604/96.01 |
| 5,681,522 A | 10/1997 | Roychowdhury |
| 5,702,439 A | 12/1997 | Keith et al. |
| 5,716,373 A | 2/1998 | Wolvek et al. |
| 5,725,513 A | 3/1998 | Ju et al. |
| 5,728,063 A | 3/1998 | Preissman et al. |
| 5,733,301 A | 3/1998 | Forman |
| 5,743,876 A | 4/1998 | Swanson |
| 5,746,644 A | 5/1998 | Cheetham |
| 5,797,878 A | 8/1998 | Bleam |
| 5,807,520 A | 9/1998 | Wang et al. |
| 5,826,588 A | 10/1998 | Forman |
| 5,843,050 A | 12/1998 | Jones et al. |
| 5,891,110 A | 4/1999 | Larson et al. |
| 6,010,521 A | 1/2000 | Lee et al. |
| 6,048,338 A | 4/2000 | Larson et al. |

| | | | |
|---|---|---|---|
| 6,139,525 A | 10/2000 | Davis-Lemessy et al. | |
| 6,245,053 B1 | 6/2001 | Benjamin | |

FOREIGN PATENT DOCUMENTS

| | | |
|---|---|---|
| EP | 0 318 919 B1 | 6/1989 |
| EP | 0 448 886 A1 | 10/1991 |
| EP | 0 452 595 A1 | 10/1991 |
| EP | 0 457 456 A1 | 11/1991 |
| EP | 0 237 564 B1 | 12/1991 |
| EP | 0 485 903 A2 | 5/1992 |
| EP | 0 594 201 A2 | 4/1994 |
| EP | 0 669 143 A1 | 8/1995 |
| EP | 0 688 576 A1 | 12/1995 |
| EP | 0 452 901 B1 | 1/1996 |
| WO | WO 93/17750 | 9/1993 |
| WO | WO 94/01160 | 1/1994 |
| WO | WO 95/09667 | 4/1995 |
| WO | WO 95/22367 | 8/1995 |
| WO | WO 96/04951 | 2/1996 |
| WO | WO 96/38193 | 12/1996 |
| WO | WO 96/39205 | 12/1996 |
| WO | WO 97/17889 | 5/1997 |
| WO | WO 00/02613 | 1/2000 |
| WO | WO 01/21381 A1 | 3/2001 |

OTHER PUBLICATIONS

Hawley's Condensed Chemical Dictionary, 1993, p. 873.
Kohan, *Nylon Plastics Handbook*, Hanser/Gardner Publications, Inc., Cincinnati, Ohio, Copyright 1995, pp. 378-387.
*Plastics Digest*, Edition 15, vol. 2, 1994, p. 2-314.

* cited by examiner

DISTAL BALLOON WAIST MATERIAL RELIEF AND METHOD OF MANUFACTURE

TECHNICAL FIELD

The present invention generally relates to the field of medical devices. More specifically, the present invention relates to intravascular balloon catheters.

BACKGROUND OF THE INVENTION

Intravascular diseases are commonly treated by relatively non-invasive techniques such as percutaneous transluminal angioplasty (PTA) and percutaneous transluminal coronary angioplasty (PTCA). These therapeutic techniques are well known in the art and typically involve the use of a balloon catheter with a guidewire, possibly in combination with other intravascular devices such as stents. A typical balloon catheter has an elongate shaft with a balloon attached proximate its distal end and a manifold attached to its proximal end. In use, the balloon catheter is advanced over the guidewire such that the balloon is positioned adjacent a restriction in a diseased vessel. The balloon is then inflated and the restriction in the vessel is opened.

Several characteristics that are important in intravascular balloon catheters include pushability, trackability and crossability. Pushability refers to the ability to transmit force from the proximal end of the catheter to the distal end of the catheter. Trackability refers to the ability to navigate tortuous vasculature. Crossability refers to the ability to cross narrow restrictions in the vasculature, such as stenosed vessels. There is an ongoing effort to provide improved balloon catheters in terms of each of these characteristics.

SUMMARY OF THE INVENTION

The present invention contributes to this ongoing effort by providing, for example, an improved balloon catheter that has a reduced amount of material in the balloon waist in order to reduce profile and increase flexibility. The reduction in profile and the increase in flexibility enhances the trackability and crossability of the balloon catheter.

DETAILED DESCRIPTION OF THE PREFERRED EMBODIMENTS

The following detailed description should be read with reference to the drawings in which similar elements in different drawings are numbered the same. The drawings, which are not necessarily to scale, depict illustrative embodiments and are not intended to limit the scope of the invention.

Figure 1:
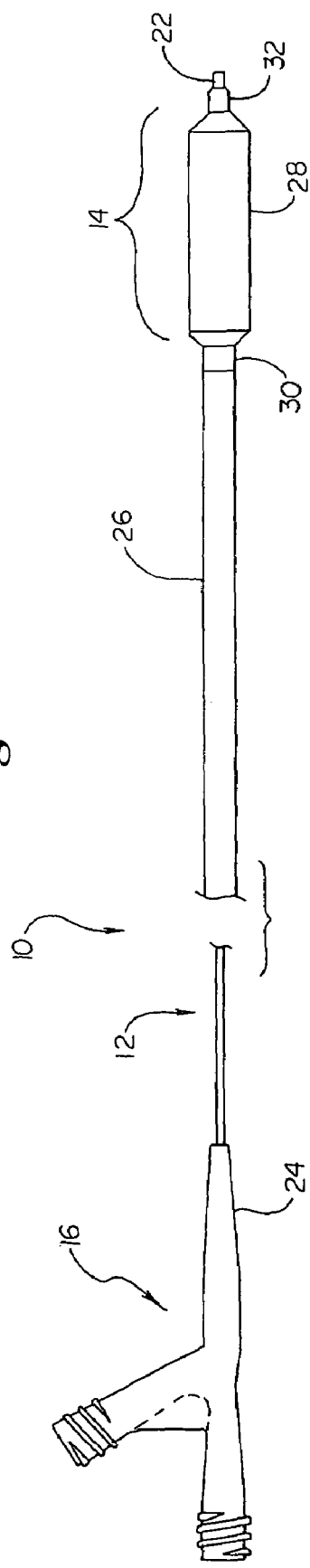
FIG. 1 is a plan view of a balloon dilation catheter in accordance with an embodiment of the present invention.

Referring now to the drawings, FIG. 1 is a plan view of an over-the-wire (OTW) balloon catheter 10, which is representative of one type of catheter that may incorporate the present invention. Other intravascular balloon catheters are additionally suitable without deviating from the spirit and scope of the present invention. For example, other intravascular balloon catheters suitable for incorporating the present invention include fixed-wire (FW) catheters and single-operator-exchange (SOE) catheters.

The balloon catheter 10 includes a shaft assembly 12 and a balloon assembly 14 connected proximate the distal end of shaft assembly 12. A conventional OTW-type manifold assembly 16 may be connected to the proximal end of the shaft assembly 12.

The shaft assembly 12 may have conventional dimensions and may be made of conventional materials suitable for intravascular navigation as in, for example, conventional angioplasty procedures. The shaft assembly 12 may be a dual lumen design or a coaxial design as shown. In a coaxial design, the shaft assembly 12 includes an inner tubular member 22 and an outer tubular member 26. The inner tubular member 22 defines a guidewire lumen, and the outer tubular member 26 is co-axially disposed about the inner tubular member 22 to define an annular inflation lumen therebetween.

At the distal end of the shaft assembly 12 is a balloon assembly 14. The balloon assembly 14 includes an expandable balloon portion 28 having a proximal balloon waist 30 and a distal balloon waist 32. The proximal balloon waist 30 connects the balloon assembly 14 to the outer tubular member 26 near its distal end by means of an adhesive and/or a thermal bond. The distal balloon waist 32, as shown best in FIG. 2, similarly connects the balloon assembly 14 to the inner tubular member 22 near its distal end by means of an adhesive bond and/or a thermal bond. This particular balloon assembly 14 arrangement allows the expandable balloon portion 28 to be in fluid communication with the annular inflation lumen defined between the outer tubular member 26 and the inner tubular member 22.

Figure 2:
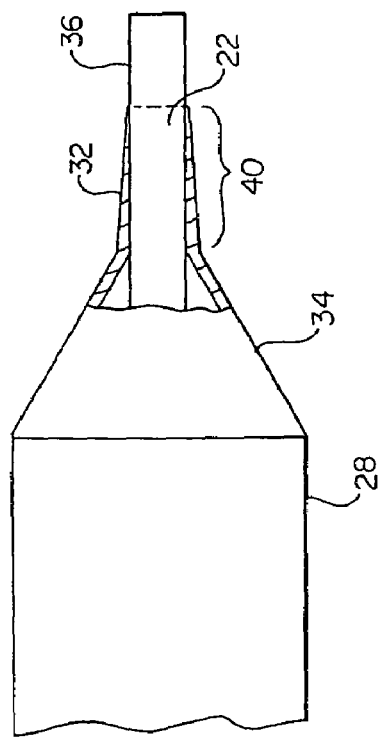
FIG. 2 is a partial cross-sectional view of a distal tip design of the catheter of FIG. 1.

FIG. 2 shows a partial cross-sectional view of the distal tip section of the catheter 10 shown in FIG. 1. The distal tip section includes the expandable balloon 28, the distal cone 34, the distal balloon waist 32 and the distal end of the inner tubular member 22. The cone 34 of the balloon assembly tapers inwardly toward the distal balloon waist 32. Generally, the thickness of the material forming the distal balloon waist 32 is similar in thickness as the material forming the distal end of the cone 34, absent further processing.

As described in detail above, the distal balloon waist 32 is connected to the inner tubular member 22 near its distal end by means of an adhesive bond and/or a thermal bond. In certain embodiments, the distal balloon waist 32 is only connected to the inner tubular member 22 which extends beyond the distal balloon waist 32. In alternative embodiments, the distal balloon waist 32 is connected to the inner tubular member 22 and a distal tip member 36. In these embodiments, the separate distal tip segment 36 extends distal of the inner tubular member 22 and the distal balloon waist 32. The separate distal tip segment 36 may comprise a soft polymeric material that allows the catheter 10 to navigate and traverse the tortuous pathways of a patient's vasculature in an atraumatic manner. In embodiments possessing a separate distal tip segment 36, both the inner tubular member 22 and the separate distal tip segment 36 may be connected to the distal balloon waist 32.

Materials suitable for the separate distal tip segment 36 include, by way of example, not limitation, a polyethylene, polyamide, or block copolymer such as PEBAX having a durometer between about 50D and 70D. In some embodiments, the distal tip 36 may comprise a polymeric material having a durometer of about 63D which is heat welded or bonded to the distal end of the inner tubular member 22. In alternative embodiments, the distal ½ to 1 mm of the distal tip 36 may be made of a different material than that of the remaining portion of the distal tip 36. In particular, the distal ½ to 1 mm may be made from a material that is more durable relative to the remaining softer distal tip material. The more durable material resists deforming or tearing when in use, such as in tracking the patient's tortuous anatomy. For example, the distal ½ mm to 1 mm may be manufactured from Marlex high-density polyethylene having a hardness of approximately 63D durometer. This distal tip material may improve the integrity of the tip region at its distal-most end.

In order to provide a smooth transition from the distal balloon waist 32 to the inner tubular member 22, or alternatively to the distal tip section 36, a taper 38 may be formed. There are numerous methods for forming the taper 38 on the distal balloon waist 32.

In one procedure, a grinding wheel is utilized to ablate the distal balloon waist 32 into a tapered end 38. The ablating wheel may be aligned so as to remove only the excess polymeric material, while not ablating any sections of the inner tubular member 22 or separate distal tip segment 36. Because this procedure may be dependent on operator skill, it may be desirable that the taper 38 only encompass a small portion of the distal balloon waist 32, as depicted in FIG. 2, to prevent improper ablation of either the distal balloon waist 32 or the inner tubular member 22.

In another embodiment, a backfilling procedure may be utilized to obtain a tapered profile 38 for the distal tip section. Similar to the ablation procedure described above, the creation of a proper taper 38 utilizing a backfilling material may be dependent on operator skill. In this procedure, an operator first applies an appropriate amount of material between the distal end of the balloon waist 32 and the distal tip section. The operator may then sculpt the backfill material to provide the desired transition between the distal balloon waist 32 and the inner tubular member 22. A taper 38 formed from such a backfilling procedure looks similar to the distal tip section depicted in FIG. 2.

In yet another embodiment, laser welding may be used to direct a focused beam of energy upon the distal end of the distal balloon waist 32. The laser eventually causes the distal end of the distal balloon waist 32 to melt and flow. The flowing polymeric material is then formed to produce a tapered end 38 similar to that depicted in FIG. 2. Flowing and forming the polymeric material to achieve a uniform and full length taper may be difficult to control and may lead to undesirable polymeric aberrations on the balloon assembly 14.

In the grinding procedure described above, only the distal end of the distal balloon waist 32 is typically tapered. As a result, a considerable amount of the material forming the distal balloon waist 32 may remain. In the backfilling procedure, more material is added upon that region of the catheter assembly. In the laser welding procedure, no material need be removed from the balloon waist 32, the material is simply allowed to reflow and formed into a taper. Since flexibility in the distal tip section is dependent upon the quantity of polymeric material in the region, a method that removes excess material from the distal balloon waist 32 would provide a reduction in profile and an increase in flexibility and, therefore, would improve the crossability and trackability of the catheter 10 as a whole.

The trackability of a particular catheter design may be analyzed in terms of the trackability of the distal portion of the catheter 10. The distal portion is the section of the catheter 10 that must track the guidewire through the small tortuous vessels of a patient's vasculature. The size of the distal tip, the flexibility of the distal tip, and the lumen diameter all influence the trackability of the catheter 10. Imparting more flexibility to the distal portion of the catheter 10, in particular, has been found to improve trackability. Increasing the flexibility within the distal tip also improves handling and navigation over a guidewire.

To maximize crossability, the distal tip may incorporate a narrow profile that includes a smooth transition from the distal tip region through the balloon assembly 14. A narrow profile enables the catheter 10 to easily pass through tight restrictions. Moreover, a smooth transition within the balloon assembly 14 reduces the occurrence of a portion of the catheter 10 becoming entangled within a deployed stent.

In a preferred procedure, the distal balloon waist 32 may be modified prior to its adherence to the catheter shaft 12. In particular, material is removed from the distal balloon waist 32 subsequent to blow molding the balloon 14 and prior to bonding the distal waist 32 to the inner tubular member 22. Material removal causes a decrease in material volume per unit length of the distal balloon waist 32 which, in turn, causes a reduction in profile of the distal waist 32 subsequent to thermal reformation. The material volume per unit length may decrease distally to impart a distally extending taper.

Figure 3:
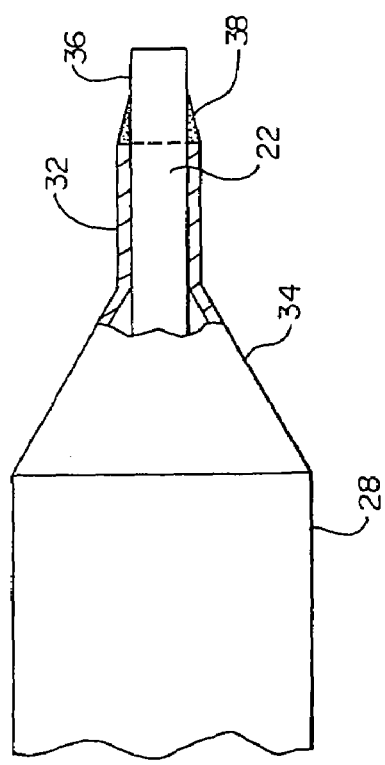
FIG. 3 is a cross-sectional view of a distal tip design of the present invention.

The material removed may be of a variety of shapes and patterns as described hereinafter. For example, the distal balloon waist 32 may have sections of material (voids) removed in predetermined patterns chosen to optimize the melt and flow phenomenon caused by thermal reformation (e.g., thermal bonding). The thermal reformation or bonding procedure melts the polymeric material of the distal balloon waist 32 and the patterned voids formed into the distal balloon waist 32 direct the flowing polymeric material and provide a place for the flowing polymeric material to pool. The pooled polymeric material is then allowed to solidify creating a uniform taper 40 along the entire length of the distal balloon waist 32, as depicted in FIG. 3. The thermal bonding process also firmly adheres the distal balloon waist 32 to the inner tubular member 22. Thus, two or three procedures (reformation, bonding and tapering of the distal balloon waist) may be completed in a single manufacturing step.

Although the patterned voids have only been described in conjunction with the distal balloon waist 32, they may additionally or alternatively be incorporated into other polymeric surfaces on a catheter assembly. For example, the patterned voids may be incorporated into the proximal balloon waist 30. Reducing the material mass between the proximal end of the balloon waist 30 and the outer tubular member 26 increases flexibility of the balloon assembly region 14. This added flexibility eases navigation and increases the trackability of the catheter 10 as a whole.

The patterned voids are also particularly useful in forming lap joints between two compatible catheter segments. A lap joint generally forms a continuous connection between a first segment and a second segment of a catheter shaft. By definition, however, the profile of a lap joint is not contiguous between the two segments. One segment is displaced over the second segment, forming a portion of catheter assembly having properties of both the first and second segments. In order to reduce the catheter shaft's profile, however, it is desirable to minimize and smooth the transition between the two segments of the lap joint. Providing the overlapping segment of a lap joint with the patterned voids of the present invention allows for reduced variance in the catheter's profile, while providing the necessary structural integrity to insure connection of the two segments.

FIGS. 4–7 show embodiments incorporating various patterned void designs of the present invention. By way of example, not limitation, the patterned void designs are shown incorporated into the material forming the distal balloon waist 32 of the catheter 10 of FIG. 1. Generally to all of the following embodiments, removal of more material from the distal end of the distal balloon waist 32 than from the proximal end of the distal balloon waist 32 provides a taper 40 as shown. As a result, often the concentration of the patterned voids is greater toward the distal end of the distal balloon waist 32 in order to provide the necessary tapering effect 40. Alternatively, larger patterned voids may be positioned toward the distal end of the distal balloon waist 32, while smaller voids are positioned at the proximal end of the distal balloon waist 32.

Figure 4:
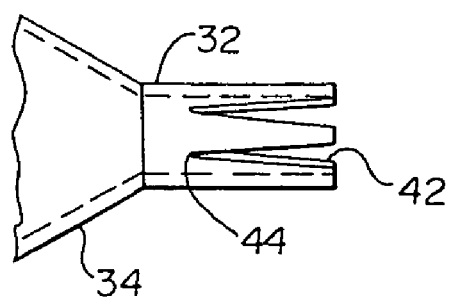
FIG. 4 is a side fragmented view of one distal balloon waist embodiment of the present invention.

Referring now to the specific patterned void design examples, FIG. 4 shows a fragmented view of one distal balloon waist 32 embodiment having balloon waist material removed in a pattern that forms a plurality of wedges 42 in the distal balloon waist 32. The plurality of wedges 42 may be evenly spaced along the entire circumference of the distal balloon waist 32. The apexes 44 of each individual wedge 42 may be positioned toward the proximal end of the distal balloon waist 32. From these apexes, material is removed as the wedge 42 fans outwardly toward the distal end of the distal balloon waist 32.

In certain embodiments, the wedges 42 may extend distally through the end of the distal balloon waist 32, as depicted specifically in FIG. 4. In an alternative embodiment, the wedges 42 stop fanning at a location proximal to the distal end of the distal balloon waist 32. This embodiment forms a series of triangular shaped voids (not shown) in the distal balloon waist 32. In yet another embodiment, the direction of the wedges 42 may be reversed from the direction depicted in FIG. 4. In this embodiment, the apex 44 of the wedge 42 is positioned at the distal end of the distal balloon waist 32 with the wedge 42 fanning outwardly proximally. The direction of the wedge 42 may be dependent on the particular method of thermal bonding utilized.

The size of the wedges 42 formed may be dependent on the particular thermal bonding process utilized. In certain embodiments, a plurality of wedges 42 having the same dimensions are cut into the distal balloon waist 32 material. In an alternative embodiment, the size of the wedges 42 is staggered. The staggered wedges 42 may have varying heights, widths, or both. Similarly, some wedges 42 may extend through the distal end of the distal balloon waist 32 while others may stop fanning at a location proximal to the distal end. Finally, a series of the wedges 42 may extend in one direction, while another set of wedges 42 may extend in the opposite direction.

In some embodiments, the wedges 42 formed are cut in a manner that entirely removes all material within the confines of the wedge-shaped form. In alternative embodiments, only a portion of the material is removed within the confines of the wedge-shaped form thereby forming a void that reduces the wall thickness of balloon waist 32 within the wedge-shaped form.

Figure 5:
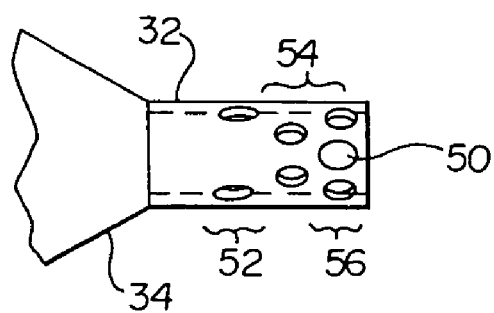
FIG. 5 is a side fragmented view of another distal balloon waist embodiment of the present invention.

FIG. 5 shows a fragmented view of another distal balloon waist 32 embodiment having balloon waist material removed in a plurality of circular formations 50. Although the circular formations 50 may be perfectly symmetrical, in alternative embodiments, the circular formations 50 may be oblong or a mix of both formations. In general, the plurality of circular formations 50 may be spaced along the entire circumference of the distal balloon waist 32. In some embodiments, the circular formations 50 are evenly spaced, whereas in alternative embodiments, the spacing is arranged in order to direct the flow of melted polymeric material into a uniform taper 40.

FIG. 5 illustrates how the concentration of circular formations 50 may increase toward the distal end of the distal balloon waist 32 to form the taper 40. A first series 52 of circular formations 50 are shown at the proximal most end being spaced a considerable amount apart from one another. The second series 54 of circular formation 50 are closer together and are more numerous than the first series 52 of circular formations 54. The third series 56 of circular formations 50 are positioned at the distal-most end of the distal balloon waist. This third series 56 of circular formations 50 is the most numerous and closely spaced of the entire set.

Similar to the previous embodiment depicted in FIG. 4, the circular formations 50 may be cut in a manner that entirely removes all material within the confines of the circular form. In an alternative embodiment, only a portion of the material is removed thereby forming a void that reduces the wall thickness of balloon waist 32 within the confines of the circular form.

Figure 6:
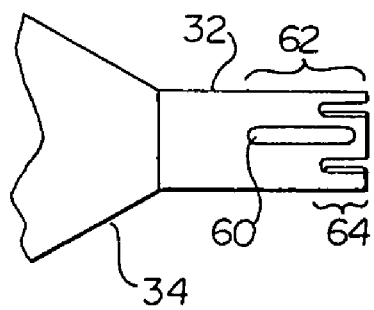
FIG. 6 is a side fragmented view of another distal balloon waist embodiment of the present invention.

FIG. 6 shows a fragmented view of another distal balloon waist 32 embodiment having balloon waist material removed in a plurality of oblong rectangular formations 60. The oblong rectangular formations 60 illustrate how a series of formations may overlap or interweave with another series of formations in order to create an area of increased material removal. In this example, two distinct series of oblong rectangular formations 60 are shown. The boundary of the first series 62 of oblong rectangular formations 60 is entirely defined within the distal balloon waist 32. The second series 64 of oblong rectangular formations 60, in contrast, extends through the distal end of the distal balloon waist 32. The two distinct series 62, 64 are spaced so that a portion of the first series 62 overlaps a portion of the second series 64. Because the two series 62, 64 of oblong rectangular formations 60 are staggered, the overlap portion is defined as that area of balloon waist material having more than one series of formations.

Staggering multiple series of formations 60 allows for greater material removal. Additionally, this particular arrangement also provides for increased flow control of molten polymeric material. In particular, the oblong rectangular formations 60 act as a series of channels that may direct and hold flowing polymeric material. Moreover, overlapping staggered formations allows for flowing polymeric material to better cross the series of channels so that the flowing polymeric material is evenly distributed along the entire circumference of the distal balloon waist 32. This added control provides for a more uniform taper 40.

Similar to the previous embodiments depicted in FIGS. 4 and 5, the oblong rectangular formations 60 may be cut in a manner that entirely removes all material within the confines of their rectangular form. In an alternative embodiment, only a portion of the distal balloon waist 32 material is removed thereby forming a void that reduces the wall thickness of balloon waist 32 within the confines of their form.

Figure 7:
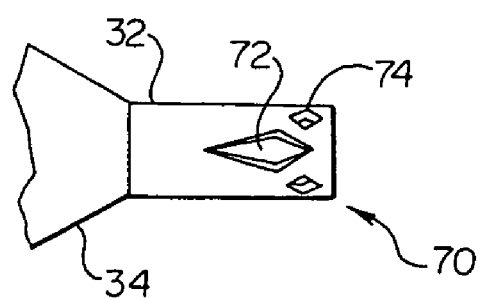
FIG. 7 is a side fragmented view of yet another distal balloon waist embodiment of the present invention.

FIG. 7 shows a fragmented view of yet another distal balloon waist 32 embodiment having balloon waist material removed in a plurality of diamond formations 70. The diamond formations 70 illustrate possible variances in size and shape of the patterned voids. Similar to the above-described embodiments, varying the size of the diamond formations 70 allows for increased control of flowing molten polymeric material. Larger formations 72 provide for greater polymeric distribution. Initially, these larger formations 72 remove more polymeric material prior to the thermal bonding process. The larger formations 72 additionally provide greater exposed surface area for flowing polymeric material to pool within. Smaller formations 74, in contrast, provide for less pooling. These smaller formations 74 are generally used to direct flowing polymeric material into larger formations 72 and to refine the distal balloon waist into the desirable uniform tapered shape 40. Similar to the previous embodiments discussed herein, the diamond formations 70 may be cut in a manner that entirely removes all material within the confines of their diamond form. In an alternative embodiment, only a portion of the distal balloon waist 32 material is removed thereby forming a void that reduces the wall thickness of balloon waist 32 within the confines of their diamond form.

Those skilled in the art will recognize that the present invention may be manifested in a variety of forms other than the specific embodiments described herein. Accordingly, departures in form and detail may be made without departing from the scope and spirit of the present invention as described in the appended claims.

What is claimed is:

1. A balloon for a balloon dilatation catheter, comprising: a balloon body having an expandable region and a balloon waist including an annular wall having a first end adjacent the expandable region, a second end and a length therebetween, the balloon waist including a plurality of voids formed in the annular wall such that the balloon waist has a material volume and a void volume created by the plurality of voids; wherein the plurality of voids are configured such that the void volume proximate the second end is greater than the void volume proximate the first end of the balloon waist.

2. A balloon for a balloon dilatation catheter as in claim 1, wherein the balloon waist has a material volume per unit length, and wherein the plurality of voids reduce the material volume per unit length.

3. A balloon for a balloon dilatation catheter as in claim 2, wherein the material volume per unit length decreases in the distal direction.

4. A balloon for a balloon dilatation catheter as in claim 3, wherein the size, number and position of the plurality of voids are selected to cause the material volume per unit length to decrease in a distal direction.

5. A balloon for a balloon dilatation catheter as in claim 3, wherein the material volume per unit length decreases in the distal direction along a majority of the length of the balloon waist.

6. A balloon for a balloon dilatation catheter as in claim 5, wherein the void volume per unit length increases in a distal direction along a majority of the length of the balloon waist.

7. A balloon for a balloon dilatation catheter as in claim 1, wherein a proximal balloon waist and a distal balloon waist each include a plurality of voids, wherein the plurality of voids are shaped and configured such that the balloon waists will have a reduced profile subsequent to thermal reformation.

8. A balloon dilatation catheter as in claim 1, wherein the plurality of voids are wedge shaped.

9. A balloon for a balloon dilatation catheter as in claim 1, wherein the plurality of voids are circular.

10. A balloon dilatation catheter as in claim 1, wherein the plurality of voids are rectangular.

11. A balloon dilatation catheter as in claim 1, wherein the plurality of voids are diamond shaped.

* * * * *